United States Patent [19]

Hall et al.

[11] Patent Number: 4,487,946

[45] Date of Patent: Dec. 11, 1984

[54] PROCESS FOR THE ISOMERIZATION OF CYCLOPROPYL KETONES TO 2,3-DIHYDROFURANS

[75] Inventors: Allen L. Hall, Amelia; Richard G. Fayter, Jr., Fairfield, both of Ohio

[73] Assignee: National Distillers and Chemical Corporation, New York, N.Y.

[21] Appl. No.: 503,952

[22] Filed: Jun. 13, 1983

[51] Int. Cl.$^3$ .................. C07D 307/28; C07D 307/30
[52] U.S. Cl. .................................. 549/474; 549/479; 549/486; 549/487
[58] Field of Search ............... 549/474, 479, 486, 487

[56] References Cited

U.S. PATENT DOCUMENTS 4,252,739  2/1981  Fayter et al. .................. 260/465 K

*Primary Examiner*—Richard L. Raymond
*Attorney, Agent, or Firm*—Kenneth D. Tremain; Gerald A. Baracka

[57] ABSTRACT

A process is provided wherein cyclopropyl ketones are readily isomerized to 2,3-dihydrofurans. The process involves the thermal rearrangement of 1,1-disubstituted-2-alkylcyclopropanes or 1,1-disubstituted-2-alkenylcyclopropanes, wherein one of the substituents in the 1-position is an acyl group, to 2,4,5-trisubstituted-2,3-dihydrofurans employing an onium compound as the catalyst.

8 Claims, No Drawings

PROCESS FOR THE ISOMERIZATION OF CYCLOPROPYL KETONES TO 2,3-DIHYDROFURANS

BACKGROUND OF THE INVENTION

1. Field of the Invention

The present invention is directed to a process for the isomerization of cyclopropyl ketones to 2,3-dihydrofurans. More specifically, the process involves the catalytic rearrangement (isomerization) of 1,1-disubstituted-2-hydrocarbylcyclopropanes, wherein one of the substituents in the 1-position is an acyl group, to 2,4,5-substituted-2,3-dihydrofurans.

2. Description of the Prior Art

A procedure for the preparation of substituted dihydrofurans is disclosed in U.S. Pat. Nos. 4,180,446; 4,198,341, 4,198,342 and 4,198,343 to Schmidt. The process involves reacting a β-alkoxycrotonic acid ester or 3,3-bisalkoxybutyric acid ester with a 1,1,1-trihalogen-4-methyl-3-pentene-2-ol or 1,1,1-trihalogen-4-methyl-4-pentene-2-ol in the presence of an acid catalyst. 2,4,4-Trimethyl-3-carbalkoxy-5-(β,β-dihalogenvinyl)-4,5-dihydrofurans are produced in the process.

Alonso et al. in *J. Org. Chem.*, 45, 4530–4532 (1980) report the rearrangement of cyclopropyl ketones to 4,5-dihydrofurans at room temperature using aluminum oxide. The rearrangement is accomplished by passing the cyclopropyl ketone in chloroform through a neutral alumina column. Whereas nearly quantitative yields of the dihydrofuran

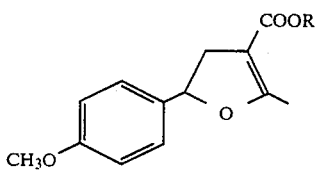

are obtained, contact times of from 24 to 72 hours are required.

Tishchenko et al. [*Chemical Abstracts*, 94, (1981), 15229w] describe the ring opening of 1-acetyl-2,2-dichlorocyclopropanes in the presence of sodium alcoholates. Depending on the amount of sodium alcoholate used, a dihydrofuran or alkyne is produced.

Dihydrofurans are also reported by Bahurel et al. in *Bull. Soc. Chim. France*, 1971 (6), 2203–8 as a by-product from the reaction of 1,4-dichlorobutene-2 and sodium ethyl acetylacetate in an alcoholic solution.

U.S. Pat. No. 4,252,739 to Fayter, Jr. et al. describes a phase-transfer process for the preparation of vinylcyclopropane derivatives by reacting an alkylating agent and an activated methylene compound using an onium catalyst and in the presence of an alkali metal compound and water. Whereas alkylation of the activated carbon atom is predominantly obtained, when the activated methylene compound contains an acyl moiety, e.g. ethyl acetoacetate, up to about 15 percent dihydrofuran by-product can be obtained as a result of alkylation at the oxygen atom of the acyl group.

Dihydrofurans have also been obtained from the rearrangement of acids or light by McGreer et al., *Can. J. Chem.*, 51 (10), 1487–93 (1973); Armitage et al., *J. Am. Chem. Soc.*, 81, 2437–40 (1959); Wilson, *J. Am. Chem. Soc.*, 69, 3002–3 (1947); and Dauben et al., *J. Org. Chem.* 34, 2301–6 (1969).

While it is known to obtain dihydrofurans from cyclopropyl ketones, it is evident from the above-mentioned references that a variety of other rearrangement products are produced depending upon the reaction conditions employed. Accordingly, it would be highly advantageous if other processes were available whereby dihydrofurans could be specifically obtained by the rearrangement of cyclopropyl ketones.

SUMMARY OF THE INVENTION

It is therefore an object of this invention to provide a process whereby a wide variety of 4,5-disubstituted-2-alkyl(or alkenyl)-2,3-dihydrofurans are readily obtained by the rearrangement (isomerization) of 1,1-disubstituted-2-alkyl(or alkenyl)cyclopropane wherein one of the substituents in the 1-position is an acyl group. This is accomplished by the present process whereby a cyclopropyl ketone is heated at a temperature in the range 60° C. to 200° C. and in the presence of 0.5 to 20 weight percent onium catalyst based on the weight of the cyclopropyl ketone. More preferably, the onium catalyst is a quaternary ammonium or quaternary phosphonium compound employed at a 2 to 15 weight percent level and the temperature is in the range 80° C. to 170° C. The quaternary ammonium and phosphonium catalysts contain at least 6 carbon atoms and correspond to the formula

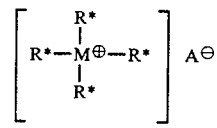

where M is nitrogen or phosphorous, R* represents a hydrocarbon radical having from 1 to 22 carbon atoms and A is halide. Particularly useful quaternary ammonium and phosphonium compounds are those where A is chloride or bromide and R* is alkyl, phenyl, $C_{1-4}$ alkyl-substituted phenyl, benzyl or $C_{1-4}$ alkyl-substituted benzyl.

DETAILED DESCRIPTION OF THE INVENTION

The process of this invention generally relates to the preparation of 2,3-dihydrofurans from the corresponding cyclopropyl ketone compound by catalytic isomerization. More specifically, the process involves the rearrangement (isomerization) of 1,1-disubstituted-2-alkylcyclopropanes of 1,1-disubstituted-2-alkenylcyclopropanes, wherein one of the substituents in the 1-position is an acyl group, to 2,4,5-substituted-2,3-dihydrofurans employing an onium compound as the catalyst. By the process it is possible to readily obtain a wide variety of 4,5-disubstituted-2-alkyl(or alkenyl)-2,3-dihydrofurans. It is also possible with the present process to treat products which contain a mixture of the vinylcyclopropane and dihydrofuran moieties to increase the amount of the dihydrofuran.

For the process, 1,1-disubstituted-2-hydrocarbylcyclopropanes, wherein one of the substituents in the 1-position is an acyl group, are employed. The 1,1-disubstituted-2-hydrocarbylcyclopropanes, which are also referred to herein as cyclopropyl ketone compounds, correspond to the general formula

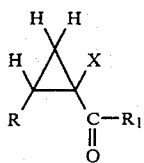

where R and $R_1$ are hydrocarbon radicals having from 1 to 24 carbon atoms and X is a carboxylate, nitrile, amide or sulfonyl group. It is evident from the formula that a wide variety of cyclopropyl ketones can be utilized in the process of this invention to prepare 2,3-dihydrofurans. The process further encompasses the use of various geometric and stereo isomers of these cyclopropyl ketones and mixtures and racemates thereof.

Hydrocarbyl groups, i.e., radicals comprised of carbon and hydrogen only, from which $R_1$ is selected can be aliphatic, cycloaliphatic or aromatic. When $R_1$ is an aliphatic group, it can be straight-chain or branched, saturated or unsaturated, and preferably contains from 1 to 12 carbon atoms. Unsaturated aliphatic radicals will generally have no more than one double bond for every four carbon atoms. Useful cycloaliphatic radicals from which $R_1$ is selected can contain from 3 to 24 carbon atoms, however, preferred cycloaliphatic radicals have from 5 to 20 carbon atoms and correspond to the formula

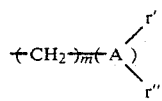

where m is an integer from 0 to 8, and more preferably 0 to 4, A represents a non-aromatic 5- or 6-membered carbon ring system, and r' and r" are hydrogen, $C_{1-8}$ alkyl, $C_{1-8}$ alkenyl, phenyl or benzyl. Particularly advantageous cycloaliphatic radicals are those wherein the moiety

is an unsubstituted or mono- $C_{1-8}$ alkyl- or alkenyl-substituted cyclopropyl, cyclopentenyl, cyclohexyl, cyclohexenyl or cyclohexa-2,4-dienyl group. If $R_1$ is an aromatic hydrocarbon group it will contain from 6 to 24 carbon atoms and may consist of a single ring or fused ring system which can one or more hydrocarbon groups substituted thereon. Especially useful aromatic radicals contain from 6 to 18 carbon atoms and correspond to the formula

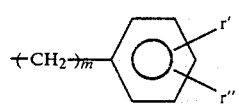

where m, r' and r" are the same as defined above. Preferred aromatic radicals include phenyl, $C_{1-8}$ alkyl- or alkenyl-substituted phenyl, benzyl and $C_{1-8}$ alkyl- or alkenyl-substituted benzyl. The ring may also contain other substituents such as halogen, hydroxy, alkoxy, carboxy, carboxylate and the like.

The hydrocarbyl radical R containing from 1 to 24 carbon atoms can be an aliphatic, cycloaliphatic or aromatic radical of the general type described above for $R_1$. Most generally, however, R is a $C_{2-8}$ aliphatic hydrocarbon radical which can be straight-chain or branched and can be saturated or unsaturated. If R is unsaturated, it generally will have no more than one double bond. Vinyl and vinylene groups are particularly useful unsaturated aliphatic radicals. The process is particularly useful for the isomerization of cyclopropyl ketones wherein R is vinyl or ethyl.

X is a carboxylate, nitrile, amide or sulfonyl group respectively having the formula

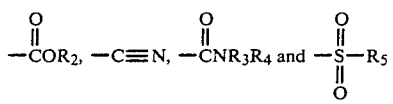

where $R_2$, $R_4$ and $R_5$ are hydrocarbyl radicals as defined above for $R_1$ and $R_3$ is hydrogen or a hydrocarbyl radical as defined above for $R_1$. For the process, it is particularly useful when the hydrocarbyl radicals from which $R_2$, $R_3$, $R_4$ and $R_5$ are selected are $C_{1-4}$ alkyl, phenyl, $C_{1-4}$ alkyl-substituted phenyl, benzyl or $C_{1-4}$ alkyl-substituted benzyl.

For the process of this invention, the cyclopropyl ketone is heated in the presence of an onium catalyst to effect isomerization. The reaction can be represented by the general equation:

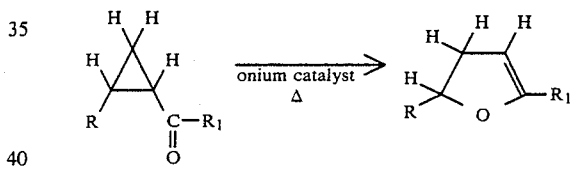

wherein X, R and $R_1$ are the same as previously defined.

Temperatures for the reaction will range from about 60° C. to about 200° C. and best results are obtained at temperatures from about 80° C. to 170° C. The onium catalyst is employed in an amount from about 0.5 to 20 weight percent, based on the cyclopropyl ketone. Most generally the onium catalyst is present from about 2 to 15 weight percent.

While it is not necessary for the reaction, the use of a solvent or diluent may be advantageous in some instances. For example, when the cyclopropyl ketone is a solid or viscous fluid, handling of the material can be facilitated by dissolving in a small amount of a suitable solvent or diluent. Any solvent/diluent should be inert and not react with the cyclopropyl ketone, 2,3-dihydrofuran or onium catalyst under the conditions employed for the reaction. It is also advantageous if the solvent has a boiling point above the reaction temperature. Lower boiling solvents can be used, however, this necessitates the use of closed reactors (autoclaves), etc. If the product is to be recovered by distillation, the boiling point of the solvent should also be such that it can be readily separated from the 2,3-dihydrofuran and any unreacted cyclopropyl ketone at the conclusion of the reaction. Useful solvents/diluents which can be used for the process include dimethyl sulfoxide; dimethyl sulfone; sulfolane; dimethyl formamide; N- methyl-2-pyrrolidone; hexamethylphosphoramide; triglyme and the like. In a preferred embodiment of the invention, the onium catalyst is dissolved in the cyclopropyl ketone and the process is conducted neat, i.e., in the absence of additional solvent or diluent.

Onium compounds useful as catalysts for this invention include quaternary ammonium and phosphonium compounds having at least 6 carbon atoms and corresponding to the formula

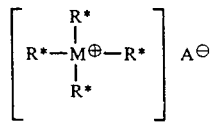

where M is nitrogen or phosphorous, R* represents a hydrocarbon radical having from 1 to 22 carbon atoms and A is halide, preferably chloride or bromide. The hydrocarbon radicals R* may be the same or different and include alkyl groups, which can be saturated, unsaturated, branched- or straight-chain, phenyl, $C_{1-4}$ alkyl-substituted phenyl, benzyl or $C_{1-4}$ alkyl-substituted benzyl. Particularly useful onium catalysts contain at least 10 carbon atoms. Illustrative onium compounds which can be used as catalysts for the process of this invention include.

tetrabutylammonium chloride;
tetrabutylammonium bromide;
dimethyldibenzylammonium chloride;
dimethyldibenzylammonium bromide;
trimethylbenzylammonium chloride;
trimethylbenzylammonium bromide;
tricaprylylmethylammonium chloride;
tricaprylylmethylammonium bromide;
tributylhexadecylphosphonium chloride;
tributylhexadecylphosphonium bromide; and the like.

The cyclopropyl ketones employed in the process should be essentially free of water and caustic. For this reason, cyclopropyl ketones obtained via classical or phase-transfer condensation are generally treated prior to use to remove water, caustic and inorganic salts. For example, in the situation where the cyclopropyl ketone is obtained via the phase-transfer process of U.S. Pat. No. 4,252,739, the resulting crude cyclopropyl ketone product may be filtered to remove insoluble inorganic salts or these salts may be dissolved in water followed by separation of the organic and aqueous phases. Residual caustic may be neutralized with dilute acid prior to filtration or dissolution of the salts. The organic phase obtained after the above-treatment may then be treated with drying agents to remove water. Most generally, however, the organic phase is stripped or distilled under reduced pressure to remove water and any organic solvent present therein.

The following examples illustrate the various aspects of this process more fully, however, numerous modifications are possible and will be evident to those skilled in the art and are within the scope of the invention.

EXAMPLE I

Methyl 1-acetyl-2-vinylcyclopropane-1-carboxylate was prepared by the reaction of 1,4-dichlorobutene-2 and methyl acetoacetate using the classical condensation procedure. For the reaction, methyl sodioacetoacetate was prepared by first reacting 36.6 grams sodium metal with 500 mls anhydrous methanol and then adding 185.6 grams of the methyl acetoacetic ester. The resulting solution was then added dropwise, at a rate sufficient to maintain reflux, to 100 grams 1,4-dichlorobutene-2 in 200 mls methanol under a nitrogen atmosphere. After addition was complete, refluxing was continued for 3 hours followed by stirring overnight at ambient temperature. The resulting reaction product (IA) was then stripped under reduced pressure after filtering to remove insoluble salts. Fractional distillation yielded 55 percent yield of a product (IB) consisting predominantly of the desired vinylcyclopropane product (boiling point 83.5° C.–85.0° C. at 4.5 mm Hg; $n_D^{22°}$ 1.4705). Nuclear magnetic resonance spectroscopy and gas chromatographic analysis of IB showed the product to consist of 85.7 percent methyl 1-acetyl-2-vinylcyclopropane-1-carboxylate and 14.3 percent 4-carbomethoxy-5-methyl-2-vinyl-2,3-dihydrofuran.

To demonstrate the rearrangement, 2 grams of IB was combined with 0.24 grams tricaprylylmethylammonium chloride and heated at 100° C. After 20 hours, the methyl 1-acetyl-2-vinylcyclopropane-1-carboxylate was reduced to 11.6 percent. The bulk of product (76.3 percent) was confirmed to be 4-carbomethoxy-5-methyl-2-vinyl-2,3-dihydrofuran. Heating for 20 additional hours increased the amount of 4-carbomethoxy-5-methyl-2-vinyl-2,3-dihydrofuran in the mixture to 83.3 percent.

When IB was heated for 20 hours by itself there was essentially no change in the amounts of methyl 1-acetyl-2-vinylcyclopropane-1-carboxylate and 4-carbomethoxy-5-methyl-2-vinyl-2,3-dihydrofuran—85.4 percent and 14.6 percent, respectively. Heating IA for 20 hours at 100° C. in a closed reactor (autoclave) gave essentially no change in the relative proportions of the methyl 1-acetyl-2-vinylcyclopropane-1-carboxylate and 4-carbomethoxy-5-methyl-2-vinyl-2,3-dihydrofuran.

EXAMPLE II

Two grams of product IB was combined with 0.16 gram dibenzyldimethylammonium chloride and the mixture heated at 100° C. Nuclear magnetic resonance spectroscopy and gas chromatographic analysis confirmed that the resulting rearranged product, obtained after 20 hours, contained 74.5 percent 4-carbomethoxy-5-methyl-2-vinyl-2,3-dihydrofuran and 25.2 percent methyl 1-acetyl-2-vinylcyclopropane-1-carboxylate.

EXAMPLE III

Product IB (2 grams) was combined with 0.30 gram tri-n-butylhexadecylphosphonium bromide and the mixture heated at 100° C. After 7 hours the amount of methyl 1-acetyl-2-vinylcyclopropane-1-carboxylate present in the mixture was reduced to 52 percent and 44 percent 4-carbomethoxy-5-methyl-2-vinyl-2,3-dihydrofuran was present. Continuing the heating for an additional 12 hours increases the amount of 4-carbomethoxy-5-methyl-2-vinyl-2,3-dihydrofuran in the mixture to about 75 percent.

EXAMPLE IV

To demonstrate the criticality of the catalyst for the rearrangement, Example III was repeated except that tetramethylammonium bromide was substituted for the tri-n-butylhexadecylphosphonium bromide at the same mole percent level. After heating for 20 hours at 100° C. the amount of 4-carbomethoxy-5-methyl-2-vinyl-2,3-dihydrofuran in the mixture was essentially unchanged.

EXAMPLE V

Essentially pure 1-acetyl-2-vinylcyclopropanecarboxanilide (melting point 104° C.-104.7° C.) was obtained by recrystallization from isopropanol and rearranged to 4-carboxanilide-5-methyl-2-vinyl-2,3-dihydrofuran in accordance with the process of this invention. For the reaction, 0.5 gram 1-acetyl-2-vinylcyclopropanecarboxaniline was combined with 89 milligrams tricaprylylmethylammonium chloride and heated at 100° C. for one hour. Analysis indicated approximately 70 percent conversion of the 1-acetyl-2-vinylcyclopropanecarboxanilide to 4-carboxanilide-5-methyl-2-vinyl-2,3-dihydrofuran. With additional heating there was a further increase in the amount of 4-carboxanilide-5-methyl-2-vinyl-2,3-dihydrofuran produced. When the reaction was repeated using 62 milligrams tetrabutylammonium chloride as the catalyst, 80 percent conversion of the 1-acetyl-2-vinylcyclopropanecarboxanilide to 4-carboxanilide-5-methyl-2-vinyl-2,3-dihydrofuran was obtained after one hour. No rearrangement was observed when the 1-acetyl-2-vinylcyclopropanecarboxanilide was heated at 100° C. in the absence of an onium catalyst.

EXAMPLE VI

Following the phase transfer procedure of U.S. Pat. No. 4,252,739, 0.53 mole ethyl hexanoylacetate, 0.66 mole 1,4-dichlorobutene-2 and 1.06 moles potassium hydroxide were reacted in a mixture of water and methylene chloride containing 0.0133 mole tricaprylylmethylammonium chloride. At the conclusion of the reaction, the reaction mixture was filtered through a sintered glass funnel to remove excess potassium hydroxide and insoluble salts formed during the reaction. The product was then washed with sulfuric acid (10 percent) and the organic layer separated and dried with magnesium sulfate. A portion of the product (119.6 grams) obtained after removal of the methylene chloride under reduced pressure and containing approximately 95 percent ethyl 2-vinyl-1-hexanoxylcyclopropane-1-carboxylate was combined with 25.6 grams tricaprylylmethylammonium chloride and heated at 110° C. under a nitrogen atmosphere with stirring. After 3 hours, the amount of 4-carbethoxy-5-n-pentyl-2-vinyl-2,3-dihydrofuran in the mixture was increased to about 41 percent. Continued heating for an additional 12 hours at 110° C. afforded a product containing approximately 87 percent 4-carbethoxy-5-n-pentyl-2-vinyl-2,3-dihydrofuran.

EXAMPLES VII-XI

Various products obtained from phase-transfer reactions similar to that of Example VI and containing varying amount of cyclopropyl ketone were rearranged in accordance with the process of the present invention. All of the products were neutralized and essentially free of insoluble salts, water and inorganic solvents. Tricaprylylmethylammonium chloride was employed as the catalyst for all of these rearrangement reactions. Details of the various reactions, including the amount of the cyclopropyl ketone and corresponding 2,3-dihydrofuran, are provided in Table I. By-products present in the starting material or obtained from the rearrangement are not identified.

TABLE I

| EXAMPLE NO. | | STARTING MATERIAL | WT. % CATALYST | REACTION TEMP. (°C.) | REACTION TIME (HRS) | | FINAL PRODUCT |
|---|---|---|---|---|---|---|---|
| VII | 77.8% | ethyl 2-vinyl-1-(4-methylpentanoyl)-cyclopropane-1-carboxylate | 20.3 | 110 | 10 | 17.4% | ethyl 2-vinyl-1-(4-methylpentanoyl)-cyclopropane-1-carboxylate |
|  | 22.2% | 4-carbethoxy-5-(3-methylbutyl)-2-vinyl-2,3-dihydrofuran |  |  |  | 82.6% | 4-carbethoxy-5-(3-methylbutyl)-2-vinyl-2,3-dihydrofuran |
| VIII | 75% | ethyl 2-vinyl-1-(5-methyl-4-hexenoyl)-cyclopropane-1-carboxylate | 19.6 | 110 | 3 | 8% | ethyl-2-vinyl-1-(5-methyl-4-hexenoyl)-cyclopropane-1-carboxylate |
|  | 25% | 4-carbethoxy-5-(4-methyl-3-pentenyl)-2-vinyl-2,3-dihydrofuran |  |  |  | 92% | 4-carbethoxy-5-(4-methyl-3-pentenyl)-2-vinyl-2,3-dihydrofuran |
| IX | 79% | ethyl 2-vinyl-1-benzoylcyclopropane-1-carboxylate | 20.0 | 150 | 2 | 7% | ethyl 2-vinyl-1-benzoylcyclopropane-1-carboxylate |
|  | 15% | 4-carbethoxy-5-phenyl-2-vinyl 2,3-dihydrofuran |  |  |  | 87% | 4-carbethoxy-5-phenyl-2-vinyl-2,3-dihydrofuran |
| X | 98% | N,N.diethyl-1-acetyl-2-vinylcyclopropanecarboxamide | 15.0 | 125 | 5 | 15% | N,N.diethyl-1-acetyl-2-vinylcyclopropanecarboxamide |
|  | 2% | 4-N,N—diethyl-carboxamide)-5-methyl-2-vinyl-2,3-dihydrofuran |  |  |  | 85% | 4-(N,N—diethyl-carboxamide)-5-methyl-2-vinyl-2,3-dihydrofuran |
| XI | 99% | 1-phenylsulfonyl-1-acetyl-2-vinylcyclopropane | 15.0 | 110 | 1.5 | 20% | 1-phenylsulfonyl-1-acetyl-2-vinylcyclopropane |
|  |  |  |  |  |  | 80% | 4-phenylsulfonyl-5-methyl-2-vinyl-2,3-dihydrofuran |

We claim:

1. A process for the rearrangement of cyclopropyl ketones to obtain 2,3-dihydrofurans corresponding to the formula

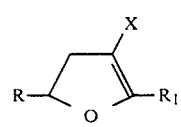

wherein R and $R_1$ are hydrocarbon radicals having from 1 to 24 carbon atoms and X is a carboxylate, nitrile, amide or sulfonyl group which comprises heating a cyclopropyl ketone, which is essentially free of water and caustic and corresponds to the formula

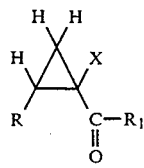

where R, $R_1$ and X are the same as defined above, at a temperature in the range 60° C. to 200° C. and in the presence of 0.5 to 20 weight percent, based on the weight of the cyclopropyl ketone, of a quaternary ammonium or quaternary phosphonium compound containing at least six carbon atoms and corresponding to the formula

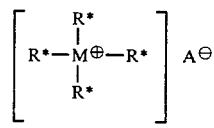

where M is nitrogen or phosphorous, R* represents a hydrocarbon radical having from 1 to 22 carbon atoms and A is halide, to effect isomerization.

2. The process of claim 1 wherein the carboxylate, amide and sulfonyl groups correspond to the respective formulae

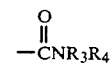

and

where $R_2$, $R_4$ and $R_5$ are hydrocarbyl radicals having from 1 to 24 carbon atoms and $R_3$ is hydrogen or a hydrocarbyl radical having from 1 to 24 carbon atoms.

3. The process of claim 2 wherein $R_2$, $R_3$, $R_4$ and $R_5$ are radicals selected from the group consisting of $C_{1-4}$ alkyl, phenyl, $C_{1-4}$ alkyl-substituted phenyl, benzyl and $C_{1-4}$ alkyl-substituted benzyl.

4. The process of claim 1 wherein R is a $C_{2-8}$ aliphatic radical and $R_1$ is selected from the group consisting of aliphatic radicals having from 1 to 12 carbon atoms, cycloaliphatic radicals having from 5 to 20 carbon atoms and aromatic radicals having from 6 to 24 carbon atoms.

5. The process of claim 1 wherein R is vinyl or ethyl.

6. The process of claim 5 wherein the temperature is in the range 80° C. to 170° C.

7. The process of claim 6 wherein the onium catalyst contains at least 10 carbon atoms with R* being an alkyl group, phenyl, $C_{1-4}$ alkyl-substituted phenyl, benzyl, or $C_{1-4}$ alkyl-substituted benzyl and A being chloride or bromide.

8. The process of claim 7 wherein the onium catalyst is present in an amount from 2 to 15 percent.

* * * * *